US005710319A

United States Patent [19]
Cosmo

[11] Patent Number: 5,710,319
[45] Date of Patent: Jan. 20, 1998

[54] PROCESS FOR THE PREPARATION OF SUBSTITUTED QUINAZOLINE-2,4-DIONES

[75] Inventor: Robert Cosmo, Darmstadt, Germany

[73] Assignee: Hoechst Aktiengesellschaft, Frankfort, Germany

[21] Appl. No.: 559,534

[22] Filed: Nov. 16, 1995

[30] Foreign Application Priority Data

Nov. 18, 1994 [DE] Germany .......................... 44 41 145.6

[51] Int. Cl.[6] ................... C07D 403/02; C07D 239/96; C07C 265/02

[52] U.S. Cl. ........................ 560/355; 544/285

[58] Field of Search ................ 544/285; 560/355

[56] References Cited

U.S. PATENT DOCUMENTS

| | | | |
|---|---|---|---|
| 4,058,612 | 11/1977 | Neustadt | 424/251 |
| 4,059,627 | 11/1977 | Kritzler et al. | 260/580 |
| 4,405,623 | 9/1983 | Ishikawa et al. | 424/251 |
| 4,506,089 | 3/1985 | Hackenberger et al. | 560/70 |
| 5,201,362 | 4/1993 | Yamagami et al. | 164/480 |
| 5,298,249 | 3/1994 | Hani et al. | 544/285 |
| 5,539,114 | 7/1996 | Cosmo et al. | 544/285 |

FOREIGN PATENT DOCUMENTS

| | | |
|---|---|---|
| 894239 | 2/1972 | Canada . |
| 0040793 | 12/1981 | European Pat. Off. . |
| 0 184 258 | 6/1986 | European Pat. Off. . |
| 0360417 | 3/1990 | European Pat. Off. . |
| 0 545 206 | 6/1993 | European Pat. Off. . |
| 0 653 423 | 5/1995 | European Pat. Off. . |
| 1804391 | 5/1970 | Germany . |
| 2345788 | 5/1974 | Germany . |
| 37 12 782 | 11/1988 | Germany . |
| 4334432 | 4/1995 | Germany . |
| 14689 | 2/1975 | Japan . |
| 1059271 | 2/1967 | United Kingdom . |

OTHER PUBLICATIONS

Chemical Abstracts, vol. 83, No. 11, Sep. 15, 1975, Columbus, Ohio, abstract No. 97348u.

Ogawa et al., "Studies on Positive Inotropic Agents. V[1]) Synthesis of 1-Heteroaroylpiperazine Derivatives", Chemical and Pharmaceutical Bulletin, 36(6), pp. 2253–2258, 1988.

Schneller et al., "Linear and Proximal Benzo–Separated Alkylated Xanthines as Adenosine–Receptor Antagonists", Journal of Medicinal Chemistry, 32(10), pp. 2247–2254, 1989.

Schneller et al., "Inhibition of Cyclic Nucleotide Phosphodiesterases from Pig Coronary Artery by Benzo–Separated Analogues of 3-Isobutyl-1-methylxanthine", Journal of Medicinal Chemistry, 29(6), pp. 972–978, 1986.

Chemical Abstract, vol. 83, No. 11, Abstract No. 97348u, p. 596, Sep. 15, 1975.

Venuti et al., "Inhibitors of Cyclic AMP Phosphodiesterase. 3. Synthesis and Biological Evaluation of Pyrido and Imidazolyl Analogues of 1,2,3,5-Tetrahydro-2-oximidazo[2, 1-b]quinazoline[1]", Journal of Medicinal Chemistry, 31(11), pp. 2136-2145, 1988.

Ishikawa et al., "Cyclic Guanidines. XVI.[1)] Synthesis and Biological Activities of Tetracyclic Imidazo[2,1-b] quinazolinone Derivatives[2)]", Chemical and Pharmaceutical Bulletin, 33(8), pp. 3336–3348, 1985.

Hammen et al., "Synthesis of 2,4-(1H,3H)-Quinazolinediones", Journal of Heterocyclic Chemistry, 24(6), pp. 1701-1703, 1987.

(List continued on next page.)

*Primary Examiner*—Matthew V. Grumbling
*Attorney, Agent, or Firm*—Connolly & Hutz

[57] ABSTRACT

The invention relates to a process for the preparation of quinazoline-2,4-diones of the formula (I)

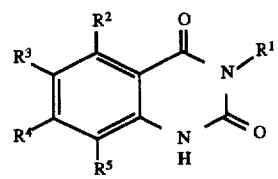

in which $R^1$ is $(C_1-C_{12})$alkyl, $(C_3-C_8)$cycloalkyl or $(C_7-C_{10})$aralkyl, it being possible for the aryl group to be substituted by one or more halogen atoms, and $R^2$, $R^3$, $R^4$ and $R^5$, independently of one another, are halogen, alkyl, alkoxy or hydrogen, which comprises reacting anthranilic acid esters of the formula (II)

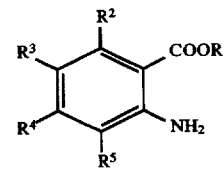

in which R is $(C_1-C_{10})$alkyl and $R^2$ to $R^5$ are as defined above, with isocyanates $R^1$—N═C═O in an aprotic reaction medium to give carbamoylanthranilic acid esters of the formula (III)

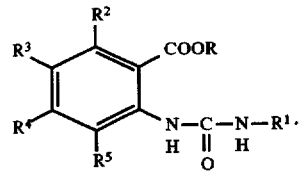

in which R, $R^1$ to $R^5$ are as defined above, and cyclizing these products in the presence of alkali metal alcoholates, alkali metal amides, alkali metal hydrides, alkaline earth metal alcoholates, alkaline earth metal amides, alkaline earth metal hydrides or tetraalkylammonium hydroxides.

1 Claim, No Drawings

OTHER PUBLICATIONS

Lespagnol, A., et al, "Derives de la benzoylene-uree", *Eur. J. Med.*, 9, pp. 263–268 (1974).

Papadopoulos, E. P., et al. "Convenient Preparation of N–Substituted 2–Amino–4H–3,1–benzoxazin–4–ones and 3–Substituted 2,4(1H,3H)–Quinazolinediones", *J. Heterocyclic Chem.*, 19, pp. 269–272 (1982).

Papadopoulos, J. Het. Chem., May 1981, vol. 18, 515–518.

Papadopoulos, J. Het. Chem. Sep. 1984, vol. 21, 1411–1414.

Papadopoulos, J. Het. Chem. Nov. 1980, vol. 17, 1553–1558.

PROCESS FOR THE PREPARATION OF SUBSTITUTED QUINAZOLINE-2,4-DIONES

Substituted quinazoline-2,4-diones of the formula (I) are interesting intermediates for pharmaceuticals and crop protection agents (U.S. Pat. No. 4,405,623; GB 1,059,271; EP 360,417).

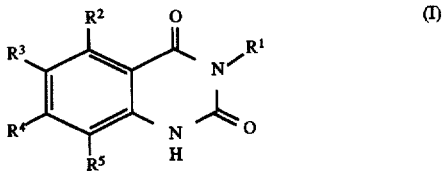

The preparation of (I) usually entails two reaction steps:

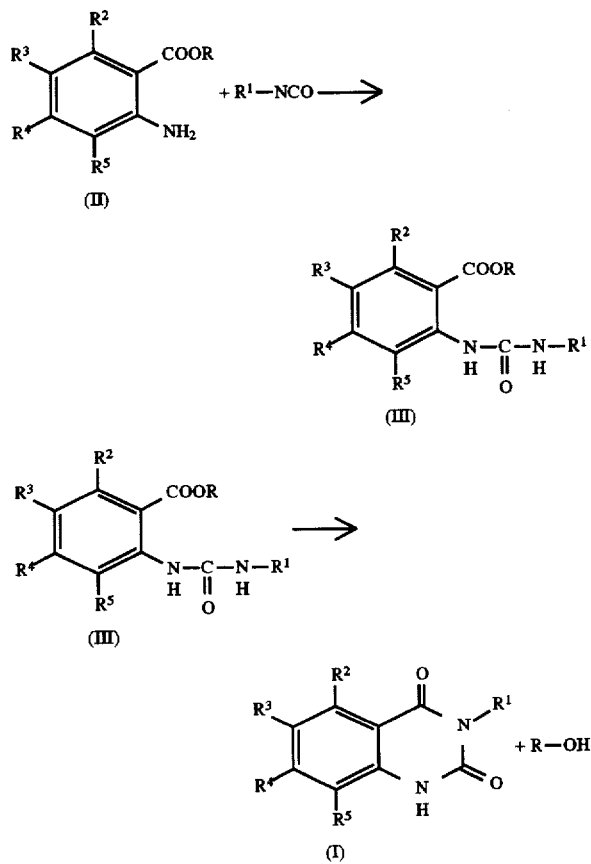

In the first step, the intermediate (III) is obtained by reacting an optionally substituted anthranilic acid or an alkyl anthranilate of the formula (II) with an isocyanate in a reaction medium which is inert to isocyanates.

In the case of anthranilic acids, N-alkylcarbamoyl-anthranilic acids (III, R =H) are obtained, which are subjected to intermediate isolation and then to cyclization in a second reaction step, for example in 10% aqueous sulfuric acid in the presence of a few drops of 95% ethanol [J. Org. Chem., 18, 1427 (1953)] to give quinazolinediones of the formula (I). In the case of N-cycloalkylcarbamoylanthranilic acids (III, R = cycloalkyl) it has already been described that the cyclization to give (I) may be carried out in a protic organic medium, such as, for example, ethanol, in the presence of an excess of strong mineral acid, such as, for example, concentrated sulfuric acid (DE-A 1,542,824).

Analogously, when the alkyl anthranilides are reacted with isocyanates, alkyl N-alkylcarbamoylanthranilates (III, R = alkyl) are obtained, which are subjected to intermediate isolation and to cyclization analogously to the above-described cyclization of the N-cycloalkyl-carbamoylanthranilic acids (III, R = cycloalkyl) [GB 2,108,495, J. Organic Chemistry, 26, p. 5238 (1961)]. In the case of the compounds III (R = alkyl or aralkyl), it is also known to carry out the cyclization to give (I) in protic media, such as, for example ethanol or methanol, in the presence of aqueous sodium hydroxide [DE-A 1,804,391, J. Heterocycl. Chem. 19 (2), p. 269 (1982)].

However, the considerable disadvantage of these preparation processes for substituted quinazoline-2,4-diones is that the preparation of the intermediate (III) is always carried out in a reaction medium different from that of the cyclization of (III) to (I).

This fact is obviously based on the preconception that the cyclization of (III) to (I) can only be carried out in protic, strongly polar media, such as, for example, in alcohols, strong mineral acids or alcoholic-aqueous alkaline media. These media, in turn, are known to be unsuitable for the preparation of (III) from (II) and aryl isocyanates, since they react very vigorously with isocyanates themselves. This fact therefore results in the use of different reaction media for the preparation of (III) and (I) and therefore necessarily to a more complicated technology and higher expenses which are naturally the result of a change of reaction medium and intermediate isolation.

Europ. J. Med. Chem., 9, p. 263 (1974) described that the reaction of methyl anthranilate (II, R = $CH_3$, $R^2$, $R^3$, $R^4$, $R^5$ = H) with alkyl isocyanates or aryl isocyanates to give N-substituted methyl carbamoylanthranilate (III, R = $CH_3$) and the subsequent cyclization to quinazoline-2,4-diones (I) can be carried out in the same reaction medium (benzene or toluene). Substoichiometric amounts of triethylamine are employed as the cyclization catalyst. The reaction can also proceed without solvents. However, the disadvantage of this process is that high reaction temperatures or long reaction times are required to convert the intermediate alkyl N-aryl- or N-alkylcarbamo-ylanthranilate (III, R = alkyl) into the quinazoline-2,4-dione (I). The products of this process generally contain the intermediate alkyl N-aryl- or alkylcarbam-oylanthranilate (III, R = alkyl) as an impurity. Complete cyclization can generally be achieved only by an excess amount of triethylamine.

The fact that heating of methyl anthranilate with alkyl isocyanates in the presence of triethylamine only results in the formation of the corresponding methyl N-alkylcarbamoylanthranilate can also be found in GB 2,108,495 and J. Org. Chem. 26, 5238 (1961). Here, cyclization to give the desired quinazoline-2,4-diones is only achieved by heating this intermediate in concentrated hydrochloric acid and ethanol.

The disadvantage, despite very short reaction times and good yields, of the abovementioned cyclization of (III) where R = alkyl to (I) in methanol or ethanol as the reaction medium with an excess of approximately 5 to 10% aqueous sodium hydroxide (DE 1,804,391); J. Heterocycl. Chem. 19 (2) p. 269 (1982) is that the first reaction product is the sodium salt of the quinazoline-2,4-dione, which must subsequently be converted into the free dione by treatment with a mineral acid or organic acid, resulting in 1 mol of the sodium salt of the mineral acid, or of the organic acid, which is undesirable and pollutes the waste water.

There was therefore a great demand for a process which allows substituted quinazoline-2,4-diones to be obtained in high yield and high purity in a technically simple manner and with low pollution of the environment.

This object is achieved by a process for the preparation of quinazoline-2,4-diones of the formula (I)

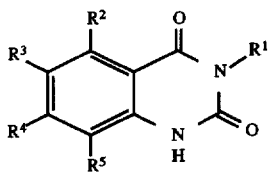

in which $R^1$ is $(C_1-C_{12})$alkyl, $(C_3-C_8)$cycloalkyl or $(C_7-C_{10})$aralkyl, it being possible for the aryl group to be substituted by one or more halogen atoms, and $R^2$, $R^3$, $R^4$ and $R^5$, independently of one another, are halogen, alkyl, alkoxy or hydrogen, which comprises reacting anthranilic acid esters of the formula (II)

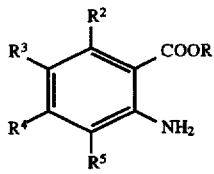

in which R is $(C_1-C_{10})$alkyl and $R^2$ to $R^5$ are as defined above, with isocyanates $R^1-N=C=O$ in an aprotic reaction medium to give carbamoylanthranilic acid esters of the formula (III)

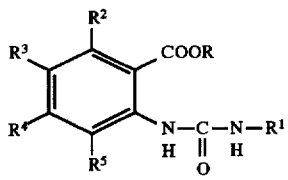

in which R, $R^1$ to $R^5$ are as defined above, and cyclizing these products in the presence of alkali metal alcoholates, alkali metal amides, alkali metal hydrides, alkaline earth metal alcoholates, alkaline earth metal amides, alkaline earth metal hydrides or tetraalkylammonium hydroxides.

The process is important for example for the preparation of compounds of the formula (I) in which $R^1$ is $(C_{1-C6})$ alkyl, $(C_3-C_6)$ cycloalkyl or $(C_7-C_8)$ aralkyl, it being possible for the aryl group of the $(C_7-C_8)$aralkyl group to be substituted by one or more halogen atoms, R is $(C_1-C_3)$ alkyl and $R^2$ to $R^5$, independently of one another, are hydrogen, $(C_1-C_3)$ alkyl, $(C_1-C_3)$ alkoxy, fluorine, chlorine or bromine. Amongst these, in turn, important compounds are those in which $R^2$ to $R^5$, independently of one another, are hydrogen, fluorine, chlorine, or methyl.

The reaction of alkyl 4-chloroanthranilate (A) with 4-bromo-2-fluorobenzyl isocyanate (B) to give alkyl N-(4-bromo-2-fluorophenylcarbamoyl)-4-chloroanthranilate (C) which is subsequently cyclized to give 3-(4-bromo-2-fluorobenzyl)-7-chloro-2,4(1H, 3H)-quinazolinedione (D) by the process according to the invention is of particular interest.

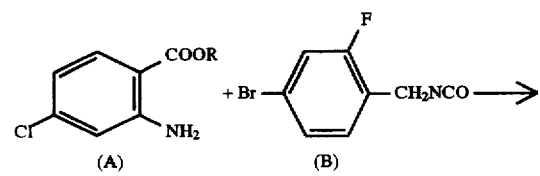

-continued

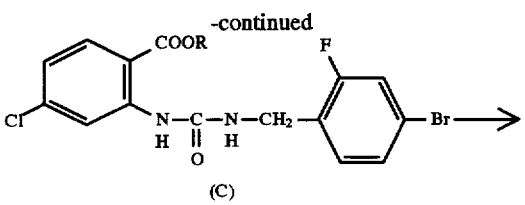

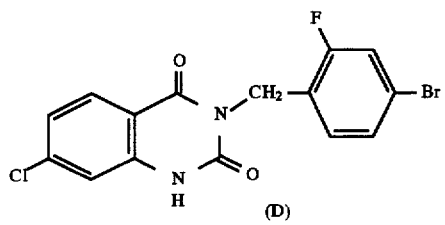

4-Bromo-2-fluorobenzyl isocyanate (B) can be prepared in high yield by reacting 4-bromo-2-fluorobenzylamine or the hydrochloride thereof with phosgene in an inert reaction medium.

The preparation of (D) has already been described in EP 218 999: here, in the first step 7-chloro-2H-3,1-benzoxazine-2,4(1H)-dione is reacted with 4-bromo-2-fluorobenzylamine in THF as the reaction medium to give 2-amino-N-(4-bromo-2-fluorobenzyl)-4-chlorobenzeunide (page 16, preparation 11), which is converted, in the second step, to (D) by carbonylation with N,N'-carbonyldiimidazole in dioxane (page 19, preparation 16, No. 4).

The process for the preparation of (D) described in EP 218,999 has substantial economic disadvantages: in the first step, the expensive 4-bromo-2-fluorobenzylamine is employed in an excess (37 mol%) based on the reactant 7-chloro-2H-3,1-benzoxazine-2,4(1H)-dione. The yield isolated is only 59%, based on 4-bromo-2-fluorobenzylamine. In the second step, the reaction to give the quinazolinedione derivative (D), the expensive reagent N,N'-carbonyldiimidazole is employed in a very high excess (300 mol%).

Compared with the process for the preparation of (D) described in EP 218,999, the process according to the invention has the following advantages: the yields from both steps, the phosgenation of the hydrochloride to (B) and the formation of (D) from (A) and (B) are high. The total yield of (D) based on the expensive 4-bromo-2-fluorobenzylamine is therefore markedly higher (79% of theory) than in the case of the process described in EP 218,999. Moreover, no expensive reagents such as N,N'-carbonyldiimidazole are required. The process according to the invention therefore involves considerably lower costs.

The cyclization of (III) to (I) proceeds with excellent yields in aprotic reaction media which, as such, are inert to isocyanates. Preferably, use is made of the same reaction media in which the compound (III) as well is prepared, such as, for example, aromatic, aliphatic or cycloaliphatic hydrocarbons, heterocycles or ketones, in particular mononuclear alkyl aromatics or alkanes and cycloalkanes which are liquid under normal conditions. In many cases, toluene and xylenes have proved themselves, either in pure form or in the form of an isomer mixture.

There is therefore the advantageous possibility of carrying out the reaction of (II) with the isocyanate to (III) and the cyclization of (III) to (I) in one and the same reaction medium at low temperatures and over very short reaction times; an intermediate isolation of (III) can be dispensed with. However, it is also possible to isolate (III), for example so as to subject it to additional purification, and subsequently to cyclize it to (I) in fresh reaction medium.

The anthranilic acid esters employed are generally the alkyl esters; substances which are employed are preferably substituted methyl anthranilates, in particular halogen-substituted methyl anthranilates.

The alkali metal alcoholates or alkaline earth metal alcoholates which are used as the base can be employed in substance or in the form of solutions in the corresponding alcohols. In many cases, the use of sodium methylate in methanol has proven itself.

If alkali metal hydrides, alkali metal amides, alkaline earth metal hydrides or alkaline earth metal amides are used, they can, again, be employed in substance or in the form of a suspension in the aprotic solvent.

The bases used are generally employed in amounts of 1 to 95 mol% based on the carbamoylanthranilic acid esters (III). The use of amounts of 1 to 20 mol%, in particular 5 to 10 mol%, has proved to be useful.

As shown in Examples 6 and 7, it was impossible to reproduce the process described in Europ. J. Med. Chem. 9, p. 263 (1974) for compounds where $R^1$ is propyl or benzyl. With triethylamine as the base, only the N-propyl- or N-benzyl-carbamoylanthranilic acid esters were obtained. No further reaction to the quinazolinediones took place. In contrast, the reaction with sodium methylate resulted in high yields of the desired compound (Examples 4 and 5).

The reaction temperature for reacting the ethyl anthranilate with the isocyanate is generally between approximately 20° C. and the boiling point of the reaction medium used, preferably in the range of between 30° and 120° C. The reaction temperature for cyclizing (III) to (I) is expediently chosen so that the alcohol being liberated is distilled off from the reaction medium; in the case of the preferred methyl or ethyl ester of (II), this means a reaction temperature above the boiling point of methanol or ethanol. However, removing the alcohol which is liberated from the reaction mixture by distillation is not crucial for successfully cyclizing (III) to (I), the cyclization reaction proceeds equally well when the alcohol being liberated is refluxed.

EXAMPLES

Example 1

Preparation of 4-bromo-2-fluorobenzyl isocyanate by phosgenation of 4-bromo-2-fluorobenzylamine Chlorobenzene (30 ml) is introduced into the reaction vessel at 60° C. and saturated with phosgene. A solution of 4-bromo-2-fluorobenzylamine (20.4 g, 0.10 mol) in chlorobenzene (40 ml) is added dropwise at 60° C. over 3 hours. At the same time, phosgene is passed in. Stirring of the batch is continued for 2 hours at 60° C., and the mixture is subsequently refluxed to remove the gases phosgene and hydrogen chloride. The batch is worked up by distillation. 15.9 g of 4-bromo-2-fluorobenzyl isocyanate (boiling point 109° C. at 4 mbar) are obtained. Yield: 69.1% of theory.

Example 2

Preparation of 4-bromo-2-fluorobenzyl isocyanate by phosgenation of 4-bromo-2-fluorobenzylamine hydrochloride A solution of 4-bromo-2-fluorobenzylamine (20.4 g, 0.10 mol) in toluene (300 ml) is saturated with gaseous hydrochloric acid at 25° C. The resulting suspension of the 4-bromo-2-fluorobenzylamine hydrochloride is heated at 100° C. Phosgene is passed in at this temperature. Stirring of the solution, which has eventually become clear, is continued at 100° C. for 1 hour, and the mixture is then refluxed to remove the gases phosgene and hydrogen chloride. The batch is worked up by distillation. 21.2 g of 4-bromo-2-fluorobenzyl isocyanate (boiling point 109° C. at 4 mbar) are obtained. Yield: 92.1% of theory.

Example 3

Preparation of 3-(4-bromo-2-fluorobenzyl)-7-chloro-2,4 (1H, 3H)-quinazolinedione A solution of 4-bromo-2-fluorobenzyl isocyanate (46.0 g, 0.20 mol) in xylene (100 ml) is metered, at room temperature, into a solution of methyl 4-chloroanthranilate (37.1 g, 0.20 mol) in xylene (250 ml). After the addition has ended, the batch is stirred at 110° C. for 2 hours. 3.60 ml of a 30% solution of methanolic sodium methylate (0.020 mol) are metered in and the mixture is stirred at 90° C. for 2 hours, during which process methanol is distilled off. 1.8 ml of 85% formic acid (0.040 mol) are subsequently added, and the mixture is stirred at 90° C. for a further hour. After cooling, the product is filtered off with suction, washed with 3×50 ml of xylene, 3×50 ml of ethanol and 3×100 ml of water, and dried. 66.1 g of 3-(4-bromo-2-fluorobenzyl)-7-chloro-2,4 (1H,3H)-quinazolinedione (yield: 86.2% of theory) of melting point 288° to 289° C. (lit. >280° C.) are obtained.

Example 4

Preparation of 3-(benzyl)-2,4(1H, 3H)-quinazolinedione

A solution of benzyl isocyanate (13.3 g, 0.10 mol) in xylene (40 ml) is metered, at room temperature, into a solution of methyl anthranilate (15.1 g, 0.10 mol) in xylene (80 ml). After the addition has ended, the batch is stirred at 110° C. for 2 hours. 1.80 ml of a 30% solution of methanolic sodium methylate (0.010 ml) are metered in, and the mixture is stirred at 90° C. for a further 2 hours, during which process methanol is distilled off. 0.9 ml of 85% formic acid (0.020 mol) is subsequently added and the mixture is stirred at 90° C. for a further hour. After cooling, the product is filtered off with suction, washed with 3×25 ml of xylene, 3×25 ml of ethanol and 3×25 ml of water, and dried. 22.2 g of 3-(benzyl)-2,4(1H,3H)-quinazolinedione (yield: 88.0% of theory) of melting point 231° to 232° C. (lit. 227° to 228° C.) are obtained.

Example 5

Preparation of 3-(propyl)-2,4(1H,3H)-quinazolinedione

A solution of propyl isocyanate (34.0 g, 0.40 mol) in xylene (100 ml) is metered, at room temperature, into a solution of ethyl anthranilate (66.1 g, 0.40 mol) in xylene (200 ml). After the addition has ended, the batch is stirred at 110° C. for 2 hours. 7.20 ml of a 30% solution of methanolic sodium methylate (0.040 mol) are metered in and the mixture is stirred at 90° C. for a further 2 hours, during which process methanol and ethanol are distilled off. 3.6 ml of 85% formic acid (0.080 mol) are subsequently added and the mixture is stirred at 90° C. for a further hour. After cooling, the product is filtered off with suction, washed with 3×25 ml of xylene, 3×25 ml of ethanol and 3×25 ml of water, and dried. 67.3 g of 3-(propyl)-2,4(1H,3H)-quinazolinedione (yield: 82.4% of theory) of melting point 190° to 191° C. (lit. 187° to 188° C.) are obtained.

Example 6

Attempt to prepare 3-(benzyl)-2,4(1H,3H)-quinazolinedione (comparison example catalyst: triethylamine)—analogously to Example 4

A solution of benzyl isocyanate (13.3 g, 0.10 mol) in xylene (40 ml) is metered, at room temperature, into a solution of methyl anthranilate (15.1 g, 0.10 mol) in xylene (80 ml). After the addition has ended, the batch is stirred at 110° C. for 2 hours. Triethylamine (1.4 ml, 1.01 g, 0,010 mol) is added. The mixture is stirred at 90° C. for a further 2 hours. The desired cyclization product 3-(benzyl)-2,4(1H,3H)-quinazolinedione cannot be detected in the reaction solution by thin-layer chromatography. After cooling, the precipitate is filtered off with suction, washed with 3×25 ml of xylene and dried. 23.1 g of methyl N-(benzylcarbamoyl) anthranilate (yield: 81.3% of theory) of melting point 140° to 141° C. (lit. 139° to 140° C.) are obtained.

Example 7

Attempt to prepare 3-(propyl)-2,4(1H, 3H)-quinazolinedione (comparison example catalyst: triethylamine)—analogously to Example 5

A solution of propyl isocyanate (34.0 g, 0.40 mol) in xylene (100 ml) is metered, at room temperature, into a solution of ethyl anthranilate (66.1 g, 0.40 mol) in xylene (200 ml). After the addition has ended, the batch is stirred at 110° C. for 2 hours. Triethylamine (5.6 ml, 4.08 g, 0,040 mol) is added. Stirring is continued at 90° C. for a further 2 hours. The desired cyclization product 3-(propyl)-2,4(1H,3H)-quinazolinedione cannot be detected in the reaction solution by thin-layer chromatography. After cooling, the precipitate is filtered off with suction, washed with 3×25 ml of xylene and dried. 67.0 g of ethyl N-(propylcarbamoyl) anthranilate (yield: 66.9% of theory) of melting point 98° to 99° C. are obtained.

I claim:
1. 4-Bromo-2-fluorobenzyl isocyanate.

* * * * *